(12) United States Patent
Kumar et al.

(10) Patent No.: US 6,486,318 B1
(45) Date of Patent: Nov. 26, 2002

(54) SINGLE POT PROCESS FOR PREPARING METAL PICOLINATES FROM ALPHA PICOLINE

(75) Inventors: Verma Pradeep Kumar, Noida (IN); Agarwal Ashutosh, Noida (IN); Bhardwaj Nikhlesha Chandra, Noida (IN); Singh Samir Kumar, Noida (IN)

(73) Assignee: Jubilant Organosys Limited, Noida (IN)

( * ) Notice: Subject to any disclaimer, the term of this patent is extended or adjusted under 35 U.S.C. 154(b) by 0 days.

(21) Appl. No.: 09/983,897

(22) Filed: Oct. 26, 2001

(30) Foreign Application Priority Data

May 24, 2001 (IN) .................................. 606/01

(51) Int. Cl.⁷ ............................. C07F 3/06; C07F 11/00
(52) U.S. Cl. .......................................... 546/5; 546/341
(58) Field of Search ....................................... 546/5, 341

(56) References Cited

U.S. PATENT DOCUMENTS

| | | | |
|---|---|---|---|
| 2,109,957 A | * 3/1938 | Dahlen et al. | 546/341 |
| 2,513,099 A | 6/1950 | Mueller | 546/341 |
| 2,522,163 A | * 9/1950 | Cislak et al. | 546/341 |
| 4,020,158 A | 4/1977 | Ashmead et al. | 424/177 |
| 4,021,569 A | 5/1977 | Abdel-Monem | 424/289 |
| 4,167,564 A | 9/1979 | Jensen | 424/177 |
| 4,315,927 A | 2/1982 | Evans | 424/245 |
| 5,677,461 A | 10/1997 | Lee | 546/263 |

* cited by examiner

*Primary Examiner*—Bernard Dentz
(74) *Attorney, Agent, or Firm*—Lowe Hauptman Gilman & Berner, LLP

(57) ABSTRACT

The present invention relates to a single pot process for the preparation of metal picolinates useful as dietary supplement from alpha picoline, said process comprising hydrosulphonation of alpha picoline with sulphuric acid; heating the reaction mixture thus obtained between the range of 150° to 210° C. followed by oxidation with any suitable oxidizing agent to obtain alpha picolinic acid sulphate, and treating the thus obtained alpha picolinic acid sulphate with a metal salt solution to obtain corresponding metal picolinate.

22 Claims, No Drawings

SINGLE POT PROCESS FOR PREPARING METAL PICOLINATES FROM ALPHA PICOLINE

FIELD OF THE INVENTION

The present invention relates to a single-pot process for the preparation of metal picolinates useful as a dietary supplement from alpha picoline source.

BACKGROUND AND PRIOR ART REFERENCES TO THE INVENTION

Metal picolinates are finding important place in dietary supplement as the source of physiologically important heavy metals, essential to both humans and animals. Body can not ingest or produce these necessary metals as such and it's deficiency leads to a variety of diseases such as Anemia correlated to iron deficiency, loss of taste and neurophysychiatric symptoms related to zinc deficiency etc. Organometallic compound esp. metallic picolinates are treated to be one of the important sources for metal supplement.

Earlier, metal picolinates were employed for the treatment of metal deficiencies, U.S. Pat. No. 4,020,158 employs metal picolinates as a food supplement in which hydrolyzed protein products were chelated with metal ions under carefully controlled reaction conditions. N.L. Jenson, U.S. Pat. No. 4,167,564 used hydrolyzed proteins as metal complexes or chelates for administering essential metals in animals. U.S. Pat. No. 4,021,569 uses zinc methionate complex for zinc supplementation.

The metal compounds with protein derivatives are more effectively assimilated than the elemental or inorganic salt forms. However, the metal co-ordination complexes with picolinic acid are directly available for absorption into the system without competition from other metals. U.S. Pat. No. 4,315,927 outlines processes for manufacturing metal picolinates viz. Iron, copper, Zinc etc. using metal salt and picolinic acid.

The anionic picolinate moiety acts as a strong chelating agent or ligand capable of binding to a cation. The cation may be a bivalent or trivalent metallic trace element essential to the nutritional value of human or other mammalian species and should exhibit binding capability with picolinic acid. These complexes are intended mainly for oral ingestion where they are generally incorporated in the food material or drinking water. Alternatively, they may be manufactured into tablets or pills with a suitable diluent or pharmaceutically acceptable carrier using any known technique.

In the prior art of preparing metal picolinates esp. chromium and zinc picolinates, a suitable metal salt namely chromium trichloride and zinc sulphate (U.S. Pat. No. 431,597) is added to a solution of picolinic acid. After the reaction is complete, the precipitated metal complex is filtered and washed with appropriate solvent and dried. U.S. Pat. No. 5,677,461 gives a modified method for producing chromium picolinate from picolinic acid at a relatively lower temperature and appropriate adjustments of pH range than mentioned in U.S. Pat. No. 4,315,927. However both the patents use chromium trichloride and picolinic acid as the starting material for manufacturing chromium picolinate. The starting material i.e. picolinic acid is not easily available. Moreover, the use of chromium trichloride generates chloride ions, which have to be removed by several washings by water or any other suitable solvent. Hence, the process of isolation of the metal picolinate from the reaction mass is cumbersome.

U.S. Pat. No. 2,513,099 details out a process for oxidizing N- heterocycle compounds containing a pyridine nucleus and an oxidizable organic group attached to the nitrogen containing aromatic nucleus by at least one carbon to carbon linkage. The process involves oxidation by reacting nitric acid with a solution containing the N- heterocycle compound and a mixture of mercury and copper compounds dissolved in sulfuric acid. This process of oxidation may normally lead to the contamination of undesired metals with the required metal picolinates. There is scanty literature available on the oxidation and recovery of the picolinic acid as such.

Thus there is a need to develop a method for producing metal picolinates from cheap raw materials and by a simpler process.

OBJECTS OF THE INVENTION

The main object of the present invention is to provide a novel single-pot process for the preparation of metal picolinates from alpha picoline source.

Another object of the present invention is to provide a novel process for oxidation of alpha picoline to picolinic acid with high purity and without any metallic contamination.

STATEMENT OF THE INVENTION

Accordingly, the present invention provides a single-pot process for the preparation of metal picolinates with high purity from alpha picoline, a cheaper raw material.

DETAILED DESCRIPTION OF THE INVENTION

Accordingly, the present invention provides a single pot process for the preparation of metal picolinates useful as dietary supplement from alpha picoline, said process comprising hydrosulphonation of alpha picoline with sulphuric acid; heating the reaction mixture thus obtained between the range of 150° to 210° C. followed by oxidation with any suitable oxidizing agent to obtain alpha picolinic acid sulphate, and treating the thus obtained alpha picolinic acid sulphate with a metal salt solution to obtain corresponding metal picolinate.

More particularly, the present invention provides a process for the preparation of metal picolinates, said process comprising: reacting alpha picoline with sulphuric acid at temperature ranging between 35° to 100° C.; heating the reaction mass to 150° to 210° C.; adding 40 to 70% concentrated Nitric acid to obtain alpha picolinic acid sulphate; adjusting the pH of the solution so as to maintain the pH in the range of 3 to 5; treating the alpha picolinic acid sulphate with a metal salt solution to obtain the corresponding metal picolinate, and purifying the resulting mass to obtain metal picolinates of high purity.

In an embodiment of the present invention, alpha picoline is alpha picoline (2-methyl pyridine).

In another embodiment of the present invention, the reaction of alpha picoline with sulphuric acid is carried out at 50° to 90° C.

In still another embodiment of the present invention, the reaction of alpha picoline with sulphuric acid is carried out at 60° to 80° C.

In yet another embodiment of the present invention, the reaction mass is heated up to a temperature of 180° to 210° C.

In still yet another embodiment of the present invention, the reaction mass is heated up to a temperature of 190° to 205° C.

In yet still another embodiment of the present invention, proper ventilation has to be provided for removal of nitric oxide fumes produced during oxidation.

In one more embodiment of the present invention, oxidation is carried out for 18 to 22 hours.

In one another embodiment of the present invention, oxidation is carried out for 20 hours.

In an embodiment of the present invention, the reaction mixture is cooled to an ambient temperature before adjusting the pH value of the reaction.

In another embodiment of the present invention, water is added before adjusting the pH value.

In still another embodiment of the present invention, the pH value is adjusted with the help of standard alkali solutions.

In yet another embodiment of the present invention, the metal salt used for the preparation of zinc picolinate is selected from the group comprising of zinc sulphate, zinc chloride, zinc acetate and zinc carbonate.

In still yet another embodiment of the present invention, zinc picolinate having 19 to 22% Zinc content is obtained.

In yet still another embodiment of the present invention, zinc picolinate having 21% Zinc content is obtained.

In one more embodiment of the present invention, the metal salt used for the preparation of chromium picolinate is selected from the group comprising of chromium nitrate, chromium chloride, chromium acetate, chromium formate, chromium carbonate and chromium sulphate.

In one another embodiment of the present invention, chromium picolinate having 12 to 12.6% Chromium content is obtained.

In an embodiment of the present invention, chromium picolinate having 12.3% Chromium content is obtained.

In another embodiment of the present invention, pure metal picolinate is obtained by filtering, washing and drying the reaction product.

In still another embodiment, the present invention provides a scope of utilizing cheaper raw material and an economical single pot synthesis with high purity product. The starting material to prepare the picolinates is alpha picoline (2-methyl pyridine), instead of picolinic acid which has been normally used in the prior arts of the synthesis and which is also much costlier than alpha picoline. Inventors have identified many other chromium salts, which can be used in place of chromium trichloride.

In yet another embodiment of the present invention, alpha picoline is reacted with sulphuric acid at temperatures ranging from 35° C. to 100° C., preferably between 50° to 90° C. and most preferably between 60° C. to 80° C. Once the addition is over, the reaction mass temperature is increased to 150° C. to 210° C., preferably between 180° to 210° C. and most preferably between 190° C. to 205° C. Nitric acid having 40 to 70% concentration is added slowly. Addition of Nitric acid leads to the evolution of Nitric oxide fume, which has to be properly vented or scrubbed. Reaction mass is then cooled to an ambient temperature and water is added followed by pH adjustment. pH is maintained between 3–5 with the help of suitable alkali solution. To the above reaction mass required metal salt solution is added to get the desired metal: picolinate. Resulting mass is then filtered washed and dried to get the pure metal picolinate.

Any one out of the following metal salts can be used for the reaction with alpha picolinic acid sulphate to get the corresponding zinc or chromium picolinates: 1. When zinc sulphate, zinc chloride, zinc acetate, zinc carbonates etc. are used the product obtained is zinc picolinate: 2. When chromium nitrate, chromium chloride, chromium acetate, chromium formate, chromium carbonate and chromium sulphate etc. are used then the product obtained is chromium picolinate.

The present invention is further described with the help of the following examples, which are given by way of illustration and therefore should not be construed to limit the scope of the invention in any manner.

EXAMPLE-1

Alpha picoline 1.0 kg was slowly added to concentrated solution of sulphuric acid under agitation. After the addition was completed the mass temperature was raised to 180° C. and 6.0 kg of 70% Nitric acid was added and the temperature was maintained at the same level for 20 hours. After the reaction was over mass was cooled to ambient temperature and three times water was added. pH of the reaction mass was adjusted to 5.0. Zinc sulphate 600 grams dissolved in water was added slowly and the whole mass was stirred till a white precipitate appeared. The precipitate was filtered washed and dried to give 800 grams of zinc picolinate having 21% Zinc content (Desired limit 19–22%)

EXAMPLE-2

Example-1 was repeated following the same procedure but zinc sulphate was replaced by zinc chloride and a product weighing 580 grams having 21.5% zinc content was obtained.

EXAMPLE-3

Picolinic acid sulphate solution (100 grams was dissolved in water 700 ml) was heated to 60°–70° C. and a solution of chromium chloride 30.0 grams was added. The whole mass was heated for 3–6 hrs and cooled to 0°–10° C. Dark red colored precipitate obtained was filtered washed and dried to give 48 grams of red colored product with chromium content 12.3% (desired chromium content 12–12.6%).

EXAMPLE-4

Example-3 was repeated but chromium chloride was replaced by chromium acetate. A pink colored product weighing 41.5 grams of chromium picolinate was isolated with 12.4% chromium content.

What is claimed is:

1. A single pot process for the preparation of zinc and/or chromium picolinates useful as dietary supplements from alpha picoline, said process comprising the steps of:
    (a) hydrosulfonation of alpha picoline with sulfuric acid at a temperature of about 35–100° C. to form a reaction mixture;
    (b) further heating the reaction mixture thus obtained to a temperature of about 150°–210° C.;
    (c) oxidizing the reaction mixture of step (b) with an oxidizing agent to obtain alpha picolinic acid sulfate at a temperature of about 50–90° C. to form a solution;
    (d) maintaining the pH of the solution of step (c) at a pH of about 3 to 5 as an acidic solution;
    (e) treating the acidic solution of step (d) with a water soluble zinc and/or chromium salt to produce a solid metal picolinate in said water; and
    (f) filtering the resulting solid metal picolinate to remove such from said water and to thereby obtain the corresponding metal picolinates of high purity.

2. The process as claimed in claim 1, further comprising, in step(c), oxidizing said reaction mixture used with an oxidizing agent comprising nitric acid.

3. The process as claimed in claim 1, wherein the reaction of alpha picoline and sulfuric acid is carried out at about 50 to 90° C.

4. The process as claimed in claim 1, wherein the reaction of alpha picoline with sulfuric acid is carried out of about 60° to 80° C.

5. The process as claimed in claim 1, further comprising heating the reaction mixture of step (c) to a temperature of about 180° to 210° C.

6. The process as claimed in claim 1, further comprising heating the reaction mixture of step (b) to a temperature of about 190° C. to 205° C.

7. The process as claimed in claim 1, further comprising removing nitric oxide fumes produced during oxidation through ventilation.

8. The process as claimed in claim 1, further comprising carrying out said oxidation for about 18 to 22 hours.

9. The process as claimed in claim 1, further comprising carrying out said oxidation for about 20 hours.

10. The process according to claim 1, further comprising cooling said reaction mixture to about an ambient temperature and then adjusting the pH of the reaction mixture to about 3 to 5.

11. The process as claimed in claim 1, further comprising adding water to the solution of step (c) before adjusting the pH of said solution.

12. The process as claimed in claim 1, further comprising adjusting the pH of the solution of step (c) by adding an alkaline solution thereto.

13. The process as claimed in claim 1, wherein said zinc salt used for the preparation of said zinc picolinate is at least ones member selected from the group consisting of zinc sulphate, zinc chloride, zinc acetate and zinc carbonate.

14. The process as claimed in claim 1, further comprising recovering zinc picolinate having about 19 to 22% by weight zinc.

15. The process as claimed in claim 1, comprising recovering zinc picolinate having about 21% by weight zinc.

16. The process as claimed in claim 1, wherein the metal salts used for the preparation of chromium picolinates are selected from the group consisting of chromium nitrate, chromium chloride, chromium acetate, chromium formate, chromium carbonate and chromium sulphate.

17. The process as claimed in claim 1, comprising recovering chromium picolinate having about 12 to 12.6% by weight chromium.

18. The process as claimed in claim 1, comprising recovering chromium picolinate having about 12.3% by weight chromium.

19. The process as claimed in claim 1, further comprising washing and drying the filtered reaction product of step (f) under conditions sufficient to produce substantially pure metal picolinate.

20. The process as claimed in claim 1, wherein the yield of zinc picolinate is about 80.0%.

21. The process as claimed in claim 1, wherein the yield of chromium picolinate is about 71.0%.

22. The process as claimed in claim 1 further comprising directly reacting the α-picolinic acid sulfate of step (d) with said water soluble metal salt(s) without substantial intermediate purification.

* * * * *